(12) United States Patent
Stenzel (10) Patent No.: US 6,540,777 B2
(45) Date of Patent: Apr. 1, 2003

(54) LOCKING STENT

(75) Inventor: Eric B. Stenzel, Tuam Co. Galway (IE)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/681,191

(22) Filed: Feb. 15, 2001

(65) Prior Publication Data

US 2002/0111671 A1 Aug. 15, 2002

(51) Int. Cl.[7] .................................................. A61F 2/06
(52) U.S. Cl. ...................................... 623/1.16; 623/1.15
(58) Field of Search ................................ 623/1.16, 1.15

(56) References Cited

U.S. PATENT DOCUMENTS 5,876,419 A * 3/1999 Carpenter et al. .......... 606/198
6,022,371 A    2/2000 Killion ....................... 606/198
6,224,626 B1 * 5/2001 Steinke ....................... 623/1.16
6,251,134 B1 * 6/2001 Alt et al. ..................... 623/1.16

FOREIGN PATENT DOCUMENTS

DE   197 28 337 A1   1/1999
WO   02/053066 A1    7/2002

* cited by examiner

Primary Examiner—Bruce Snow
(74) Attorney, Agent, or Firm—Vidas, Arrett & Steinkraus (57) ABSTRACT

A stent may be constructed to have at least one lockable cell which includes a first locking member and a second locking member. The first and second locking members are movable between a first position in which they are not locked together to a second position in which they are locked together and impart increased scaffolding strength to the stent.

44 Claims, 11 Drawing Sheets

FIG. 17

LOCKING STENT

BACKGROUND OF INVENTION

The use of stents in bodily lumen is well known. A stent is typically delivered in an unexpanded state to a desired location in a bodily lumen and then expanded. The stent may be expanded via the use of mechanical device such as a balloon or the stent may be self-expanding.

Because a stent often must be delivered through tortuous anatomy, it is desirable for the stent to be flexible. It is also desirable for the stent to exhibit high scaffolding in the expanded state. In general, however, as stent flexibility is increased, scaffolding is decreased and similarly, as scaffolding is increased, flexibility is decreased.

There remains a need for a stent having a high degree of flexibility in the unexpanded state and high scaffolding in the expanded state.

All US patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

SUMMARY OF INVENTION

In one embodiment, the invention is directed to stents comprising a plurality of interconnected cells where at least one of the interconnected cells is a lockable cell. The lockable cell includes a first locking member and a second locking member disposed opposite the first member. The first and second locking members are movable between a first position in which they do not lock with one another to a position in which they lock with one another.

The first locking member may be a pincer member comprising a first arm and a second arm and the second locking member may be a tongue. The first and second arms are movable between a first position in which they do not grip the tongue and a second position in which they grip the tongue. Desirably, the pincer members are directly opposite the tongues. Also desirably, the first and second arms are in the first position when the stent is in the unexpanded state and in the second position when the stent is in the expanded state. The stent may comprise a plurality of such cells arrangable in rows, columns or any other suitable arrangement. Adjacent lockable cells may have one or more walls in common or may have no walls in common. Individual lockable cells may comprise a single pincer member and tongue or multiple pincer members and tongues. The clampable cell may even include pincer members which are constructed and arranged to clamp other pincer members. The pincer member(s) and tongue(s) may extend from the proximal and distal ends of the cell or vice versa or may extend from sidewalls of the cell extending between the proximal and distal ends of the cells.

The first and second locking members may also be first and second interlocking members which are constructed and arranged to interlock with one another when the cell is locked.

The invention is also directed to stents comprised of a plurality of interconnected bands where at least one of the interconnected bands has a first locking member extending therefrom toward an adjacent band and a second locking member extends from an adjacent band. The first and second locking members are movable from a first position in which they do not lock with one another to a second position in which they lock with one another.

The first locking member may be a pincer member extending from a band toward an adjacent band. The pincer member has a first arm and a second arm. A tongue extends from the adjacent band. The first and second arms are movable between a first position in which they do not grip the tongue and a second position in which they grip the tongue. Desirably, the pincer members are directly opposite the tongues. Also desirably, the first and second arms are in the first position when the stent is in the unexpanded state and in the second position when the stent is in the expanded state. The pincer members and tongues may be placed anywhere along the bands. Desirably, the pincer members extend from peaks on bands and the tongues extend from a troughs on a adjacent bands. At least one pair of adjacent bands has at least one pincer member and one tongue extending therefrom. Additional pincer members and tongues may be provided between adjacent bands. Adjacent bands may include pincer members which grip other pincer members. The bands may desirably be circumferential bands, substantially longitudinal bands or helical bands.

The first and second locking members may also be first and second interlocking members extending from adjacent bands, the interlocking members constructed and arranged to interlock with one another upon locking of the cell.

In another embodiment, the invention is directed to stents comprising a plurality of interconnected cells where at least one of the interconnected cells is a lockable cell. The lockable cell includes a first locking member and a second locking member. The second locking member is constructed and arranged to lockingly engage the first locking member on expansion of the stent. Desirably, the first and second locking members clamp together or interlock with one another.

In yet another embodiment, the invention is directed to stents having a plurality of interconnected bands, where at least one of the interconnected bands has a first locking member extending therefrom toward an adjacent band and where the adjacent band has a second locking member which is constructed and arranged to lockingly engage the first locking member on expansion of the stent. Desirably, the first and second locking members clamp together or interlock with one another. Any suitable type of band may be used in the inventive stents. Desirably, each band is serpentine having alternating peaks and troughs, with the peaks extending in a distal direction and the troughs extending in a proximal direction. Bands having other geometric patterns that provide desirable contraction and expansion properties may be used as well. The bands may desirably be circumferential bands, substantially longitudinal bands or helical bands.

DETAILED DESCRIPTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

Figure 1:
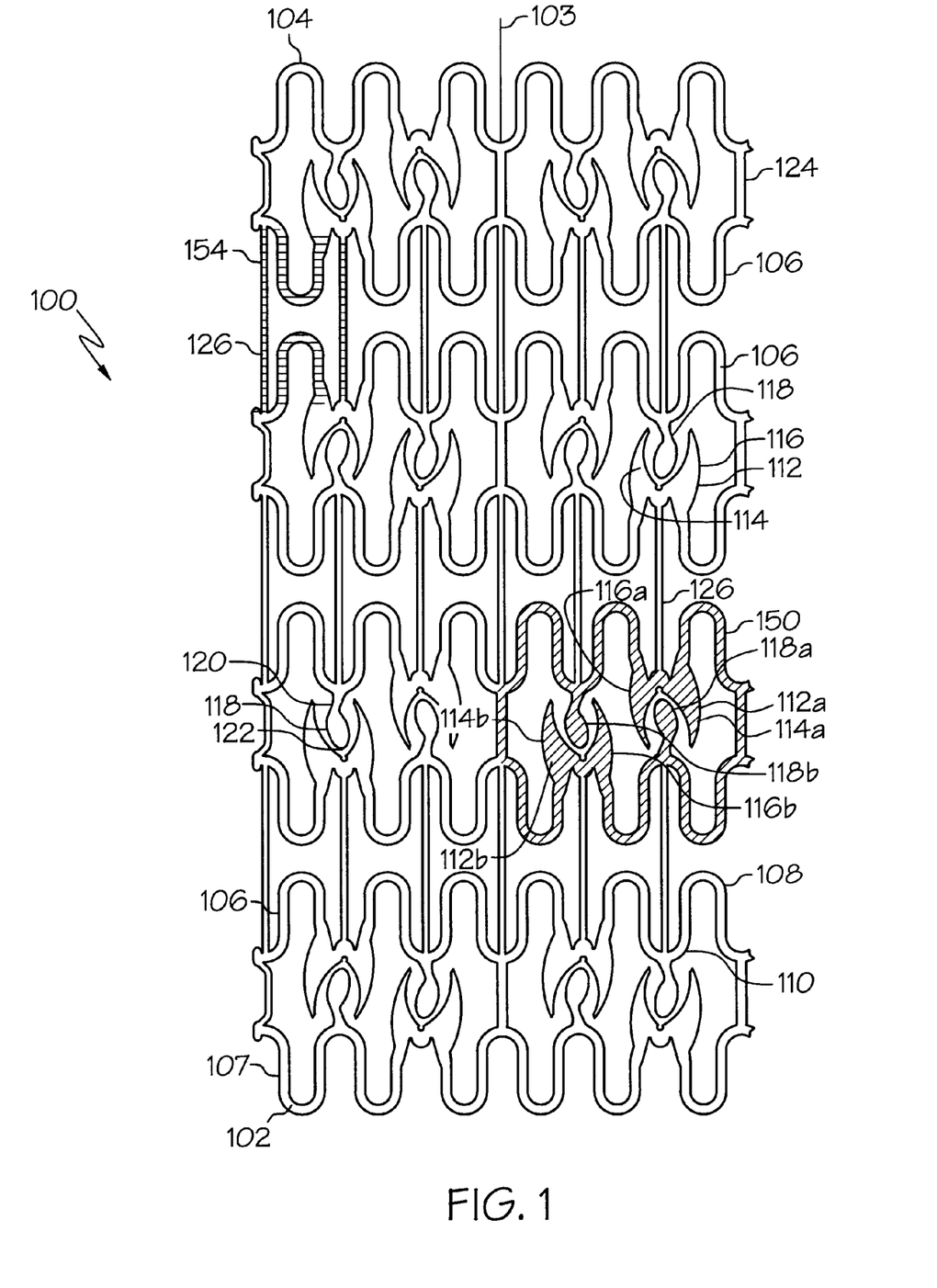
FIG. 1 illustrates a plan view of an expandable stent in accordance with the present invention.
Figure 2:
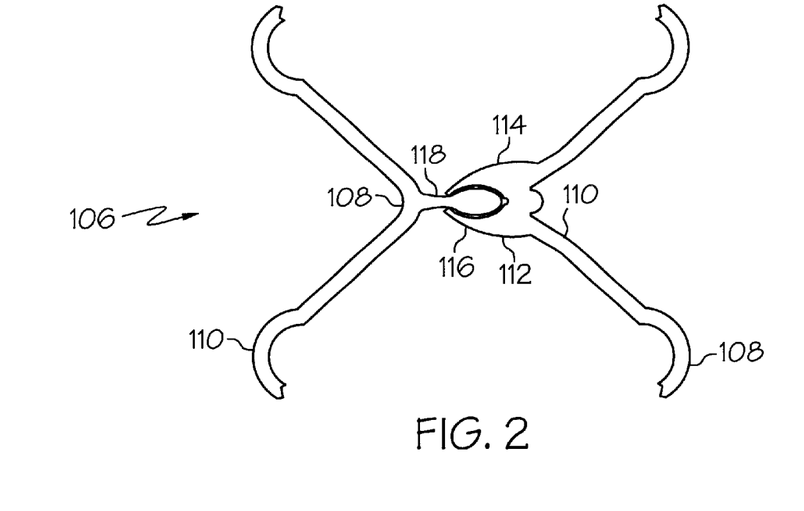
FIG. 2 shows a pincer member and tongue which may be used in an inventive stent.

FIG. 1 illustrates an expandable stent 100 having a proximal end 102 and a distal end 104 and a longitudinal axis 103. The stent comprises a plurality of interconnected circumferential serpentine bands 106. Each band 106 has alternating peaks 108 and troughs 110. The peaks are oriented in the distal direction and the troughs are oriented in the proximal direction. Each band 106 has a plurality of pincer members 112 extending therefrom. Each pincer member 112 comprises a first arm 114 and a second arm 116. Opposite each pincer member 112, a tongue 118 extends from an adjacent band. Tongue 118 includes a narrower neck portion 120 and a wider, bulbous head portion 122 which facilitates gripping action between the pincer member and the tongue. As the stent is expanded, as shown in FIG. 2, first arm 114 and second arm 116 move toward each other and grip tongue 118 in an locking relationship. The stent in the expanded state desirably exhibits greater scaffolding strength than in the unexpanded state.

Stent 100 further comprises first interconnecting members 124 and second interconnecting members 126. First interconnecting members 124 join together adjacent bands whose pincer members and tongues face each other. Second interconnecting members 126 join together adjacent bands which do not have any pincer members and tongues facing each other.

Figure 3:
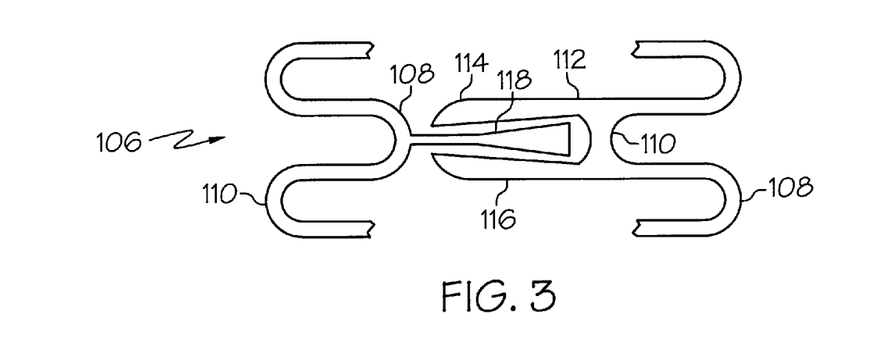
FIGS. 3 and 4 show a portion of an inventive stent with a pincer member and tongue prior to expansion and following expansion of the stent.
Figure 4:
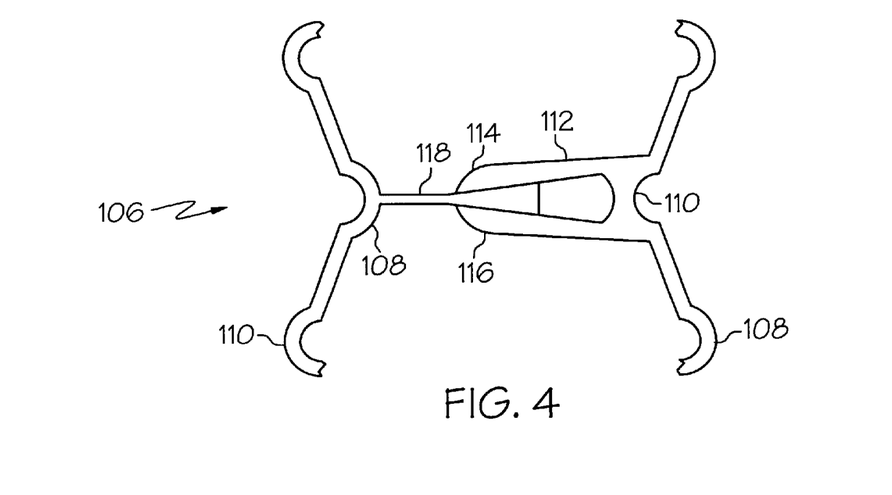

The invention also contemplates providing other tongue and pincer combinations. An example of a tongue with a triangular head is shown at 118 in FIGS. 3 (prior to expansion) and 4 (following expansion). Pincer member 112 is shaped such that in the expanded state, the pincer can grip the tongue in a locking relationship.

Figure 5:
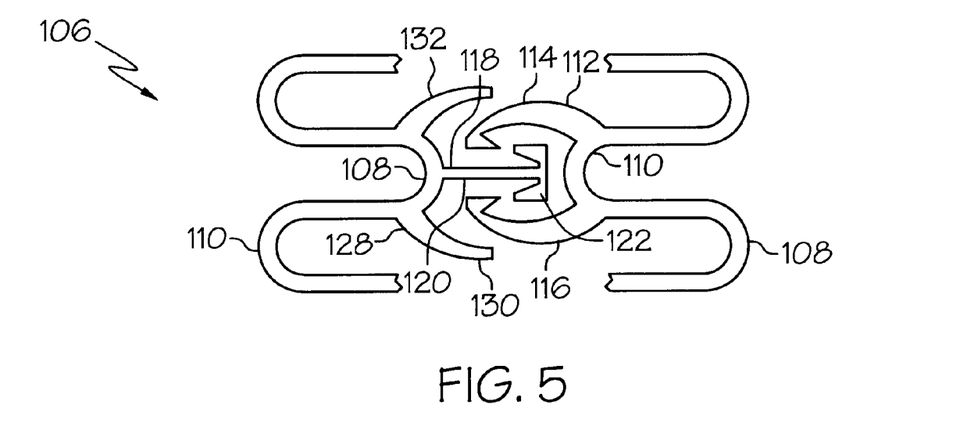
FIGS. 5 and 6 show a portion of an inventive stent with a pincer member and tongue from a stent prior to expansion and following expansion of the stent.
Figure 6:
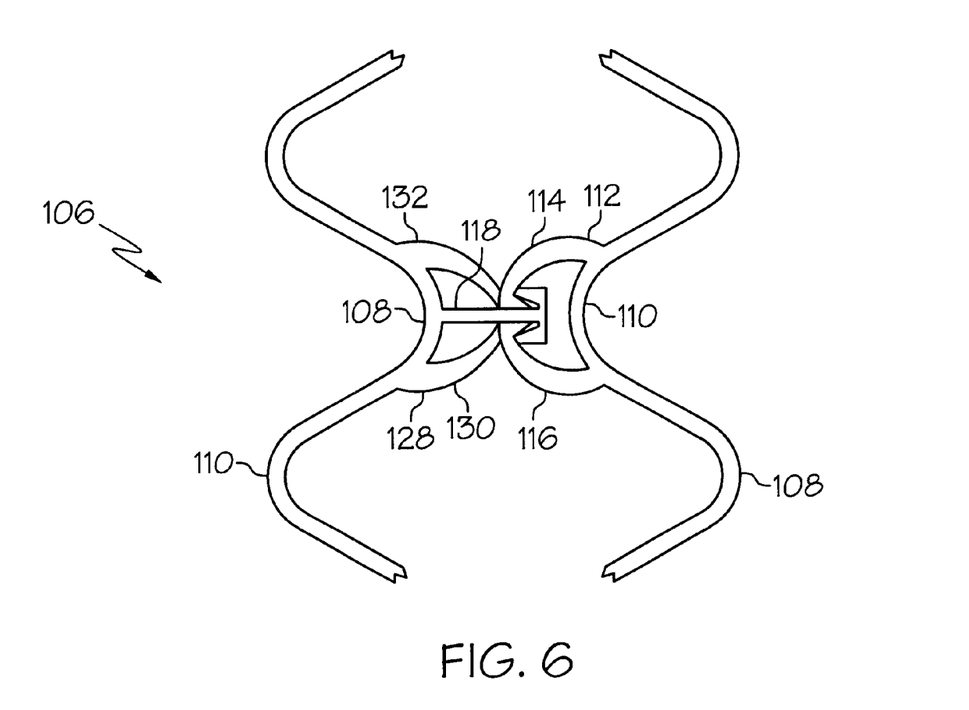
Figure 7:
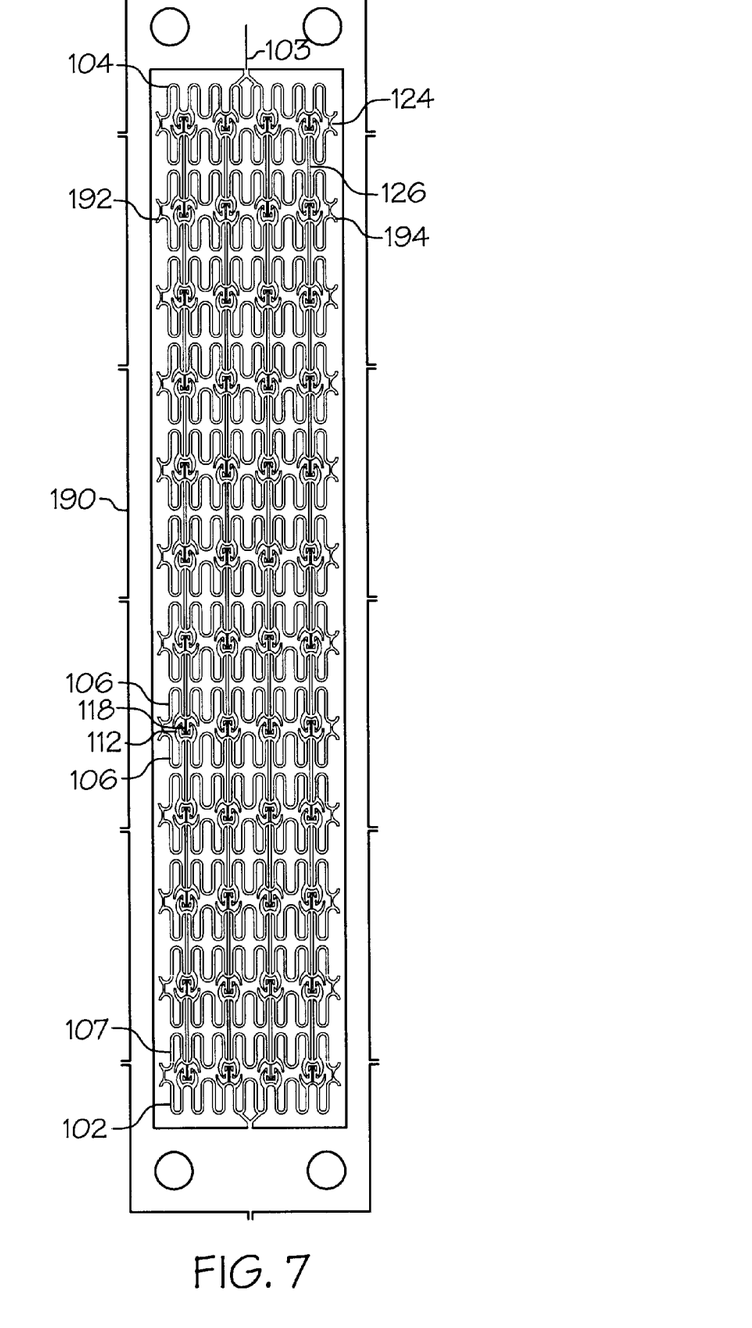
FIG. 7 shows a plan view of an inventive stent with interlocking members as shown in FIGS. 5 and 6.

Yet another example of a tongue is shown in FIGS. 5, 6 and 7. Tongue 118 is T-shaped. The first arm 114 and the second arm 116 of pincer member 112 are shaped so as to cooperate with tongue 118 allowing pincer member 112 and tongue 118 to lockingly engage one another when the stent is expanded. FIG. 7 shows a flat pattern of a stent having the locking members shown in FIGS. 5 and 6.

The flat pattern stent of FIG. 7 is shown still attached to the surrounding material 190 from which it was cut. Prior to use, the flat pattern stent must be severed from surrounding material 190 and rolled to form a tube. Edges 192 and 194 may be welded together or otherwise affixed to one another.

The embodiment of FIGS. 5–7 further differs from the embodiments of FIGS. 1–4 in that a double clamping mechanism is provided. Specifically, a second pincer member 128 comprising first 130 arm and second arm 132 is provided opposite pincer member 112. As the stent expands, the arms of the second pincer member and grip tongue 118 providing additional scaffolding strength to the stent and additional strength to the joint.

Figure 8:
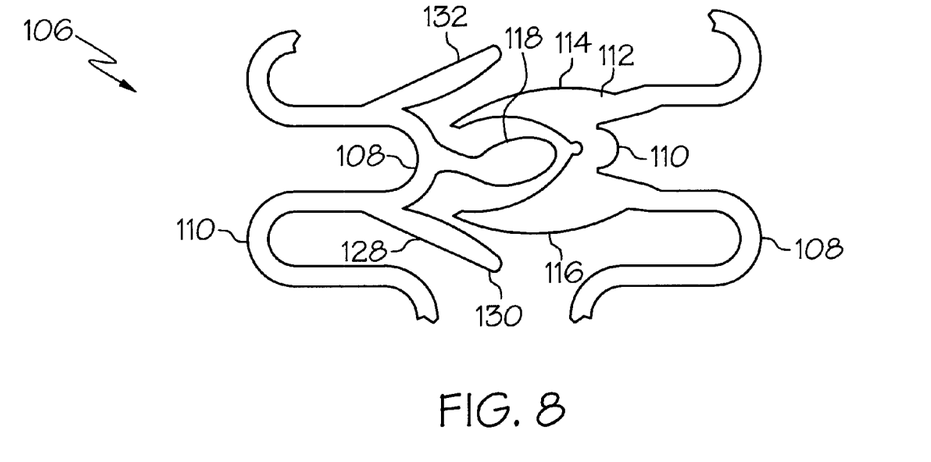
FIGS. 8 and 9 show a portion of an inventive stent with a pincer member and tongue prior to expansion and following expansion of the stent.
Figure 9:
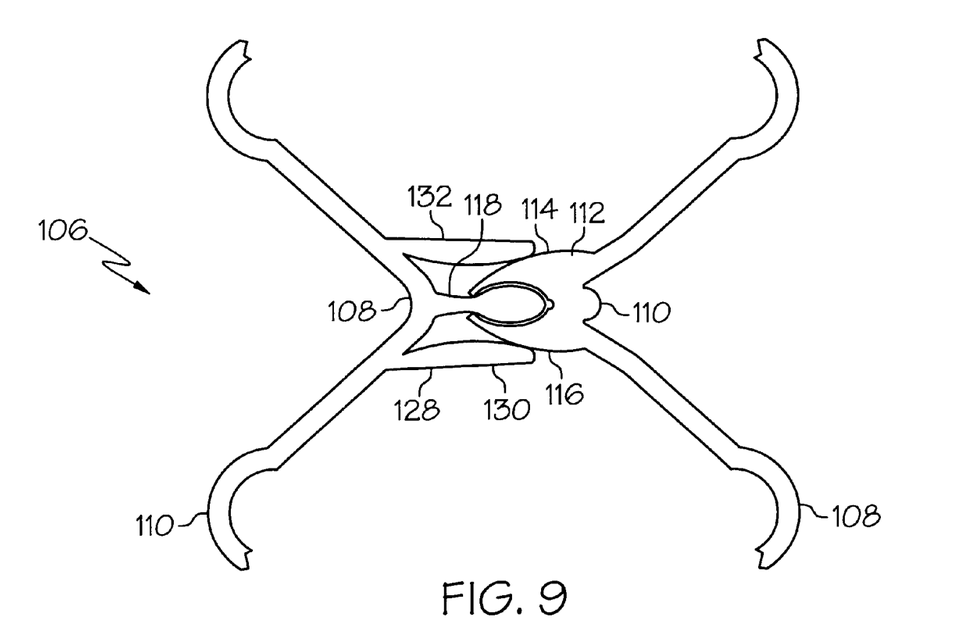

As shown in FIGS. 8 and 9, first arm 130 and second arm 132 of second pincer member 128 may be long enough so that on expansion of the stent they grip arms 114 and 116 of first pincer member 112 in an locking relationship.

In all of the above embodiments, all of the first and second interconnecting members are shown as being straight. The invention also contemplates the use of curved interconnecting members in place of or in addition to straight interconnecting members. Moreover, the invention contemplates using interconnecting members whose first and second ends are circumferentially offset relative to one another. An example of such an interconnecting member is disclosed in copending, commonly assigned U.S. application Ser. No. 08/511076. Such an interconnecting member may be linear or curved. Examples of interconnecting members are shown at 126a–d in FIG. 10.

The number of first and second interconnecting members extending between adjacent bands may also be varied. A minimum of one interconnecting member between adjacent bands is necessary. Additional interconnecting members may be provided so that a plurality of first interconnecting members and/or a plurality of second interconnecting members are present.

In the embodiment of FIG. 1, the first and second interconnecting member are of different lengths. The invention also contemplates interconnecting the bands of the stent with only a single type of connector.

Other variations that fall within the scope of the invention include varying the location of the first and second interconnecting members along the bands. In the embodiment of FIG. 1, each second interconnecting member 126 extends distally from a trough 110 on a band 106 to a peak 108 on an adjacent band 106 while each first interconnecting member 124 extends distally from a peak 108 on a band 106 to a trough 110 on an adjacent band 106. The invention also contemplates other arrangements of the first and second interconnecting members between adjacent bands. For example, the second interconnecting members may extend distally from a peak on a band to a trough on adjacent band and the first interconnecting members may extend distally from a trough on a band to a peak on an adjacent band. The first and second interconnecting members may extend from any other position along a band in-between a peak and a trough as well.

The phase arrangement between adjacent bands may be that shown in FIG. 1 or may be any other phase arrangement. Adjacent bands may be in phase with one another or may be out of phase from one another by any amount.

More generally, the invention is directed to a stent comprised of a plurality of interconnected bands where at least one of the interconnected bands has a first locking member extending therefrom toward a second locking member extending from an adjacent band.

Desirably, the first locking member is a pincer member and the second locking member is a tongue. The pincer member has first and second arms which are movable between a first position in which they are not in contact with the tongue or in which they are in slight contact with the tongue, for example, in the crimped state, and a second position in which they grip the tongue. Where more than one pincer member and tongue combination is included in the stent, the pincer member and tongue combinations may be regularly distributed throughout the stent or randomly distributed. Pincer members may be provided on all of the bands or only on some of the bands. The stent of FIG. 1 is arranged so that every other pair of adjacent bands may be locked together.

The first and second locking members may also be first and second interlocking members. To that end, the invention is also directed to stents which include one or more cooperating locking members. The stent of FIG. 1 may be modified by replacing the pincer members 112 and tongue 118 with the female 112 and male 118 interlocking members shown in FIG. 10. The operation of the interlocking members of FIG. 11 is shown in FIG. 12. As the stent expands, female interlocking member 112 and male interlocking member 118 frictionally engage one another thereby imparting additional rigidity to the stent. The interlocking members of FIGS. 11 and 12 are similar to those shown in FIGS. 5 and 6, differing in that the interlocking members of FIGS. 11 and 12 lack the clamping action of the locking members of FIGS. 5 and 6.

The invention is not limited to the specific interlocking shape shown in FIGS. 11 and 12. The interlocking members may be provided in a host of other shapes within the spirit of the present invention.

The invention is also directed to stents having a proximal end and a distal end, comprising a plurality of interconnected cells where at least one of the interconnected cells is a lockable cell. Desirably, the lockable cell is clampable or interlocks.

An embodiment of such a stent comprising a plurality of lockable cells which may be clamped is shown in FIG. 1. Clampable cell 150 is shown hatched in FIG. 1. Each clampable cell 150 includes a first pincer member 112a comprising a first arm 114a and a second arm 116a and a tongue 118a and a second pincer member 112b comprising a first arm 114b and a second arm 116b and a tongue 118b. The operation of the pincer member and tongue has been discussed above. Tongue 118a and pincer member 112a face one another as do tongue 118b and pincer member 112b. First pincer member 112a is situated on the distal end of the cell and second pincer member 112b is located on the proximal end of the cell. Other arrangements are possible as well. For example, both pincer members may be situated on the same side of the cell at either the distal end or the proximal end of the cell. Moreover, the clampable cell may comprise any number of pincers ranging from a single pincer member to two, three, four, five, six or more pincer members. Where multiple pincers are present, the pincers may be circumferentially displaced relative to one another and/or the pincers may be arranged as discussed above with respect to FIGS. 5 and 6. Other pincer member and tongue combinations, including those disclosed above may be used in the clampable cell.

In the stent of FIG. 1, lockable, clampable cells 150 are arranged in rows. Adjacent rows of clampable cells are joined together by second interconnecting member 126. Stent 100 also comprises non-clampable cells 154, arranged in rows.

The invention contemplates providing the lockable cells in any other arrangement, random or otherwise. A single lockable cell per row may be provided or multiple clampable cells per row may be provided. Every row may include lockable cells or only some of the rows may include lockable cells. In one embodiment of the inventive stent, every other row of cells is lockable. Rows of lockable cells may alternate with rows of non-lockable cells. In another embodiment of the invention, at least one row of lockable cells is provided at one of the distal end of the stent and the proximal end of the stent. In yet another embodiment of the invention, at least one row of lockable cells is provided between the proximal and distal ends of the stent. The invention also contemplates stents having rows which include lockable cells and non-lockable cells.

Figure 13:
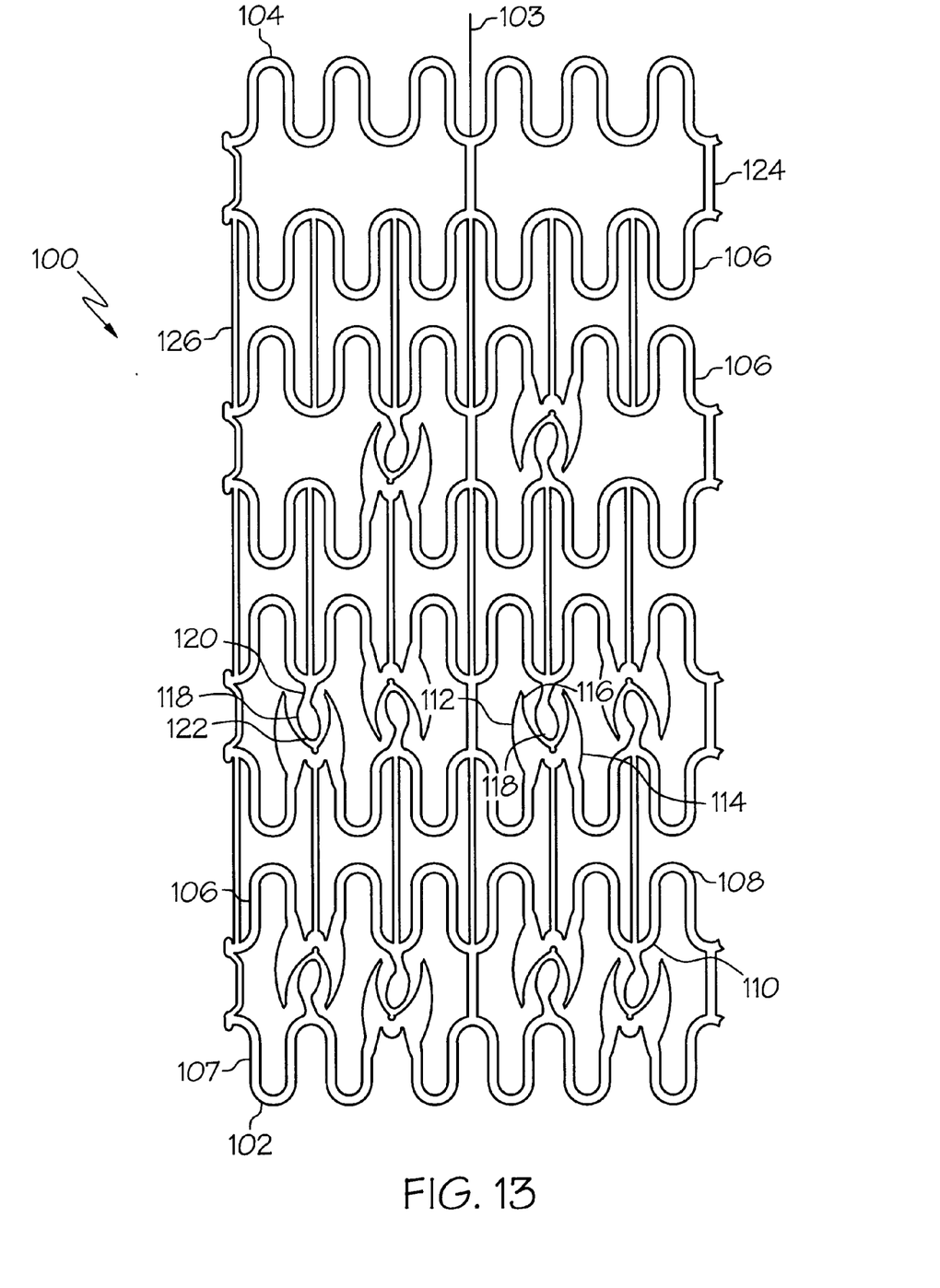
FIG. 13 illustrates a plan view of another inventive stent.

The rigidity of the inventive stents in the expanded state may be controlled by suitably arranging the lockable cells. For example, where a stent with rigid ends and a more flexible middle portion is desired, the lockable cells may be disposed only at the ends of the stent. Similarly, a stent with more flexible ends may be achieved by providing locking cells only between the ends of the stent. A stent with increasing rigidity along its length may be provided by increasing the number of lockable cells per row along the length of the stent or by increasing the number of locking members such as pincer members and tongues per row of cells as shown in FIG. 13. In the stent of FIG. 13, the number of pincer members 112 and tongues 118 increases from one end of the stent to the other end. Where it is desirable to provide more rigidity to the stent in the unexpanded state, selected locking members may be replaced by straight connectors.

Figure 14:
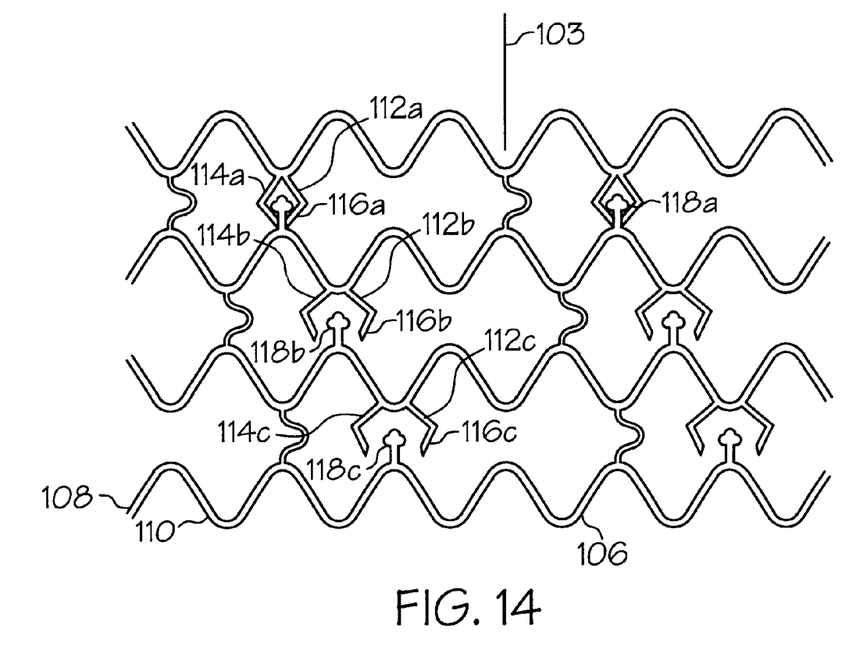
FIG. 14 illustrates a plan view of another inventive stent.

The inventive stents may also be provided with a plurality of different locking members which lock upon varying degrees of expansion of the stent. As shown in FIG. 14, this may be achieved by varying the displacement between the arms of the pincer members. Arms 114a and 116a of pincer 112a are closer together than arms 114b and 116b of pincer 112b, which, in turn, are closer together than arms 114c and 116c of pincer 112c. A similar effect may be achieved by maintaining the separation between the arms constant, but altering the width of the arms in various of the pincers. Moreover, the inventive stents may contain several differently shaped pincer members and/or tongues.

The invention also contemplates lockable cell structures other than those shown in FIG. 1. For example, the proximal and distal ends of the cells may comprise serpentine structures of different wavelengths and/or amplitudes. Moreover, the proximal and distal ends of the cells need not be serpentine. The proximal and distal ends of the cells may be of any other geometric shape which provides suitable expansion and contraction properties.

In place of the straight longitudinal sections 124 of the lockable cells, the lockable cells may also include side walls which are curved and generally longitudinal. The cells may include side walls which are generally oblique to the longitudinal axis of the stent.

The invention is also directed to stents have at least one lockable cell. The lockable cell may comprise a pincer member and tongue and/or a first interlocking member and a second interlocking member.

Figure 10:
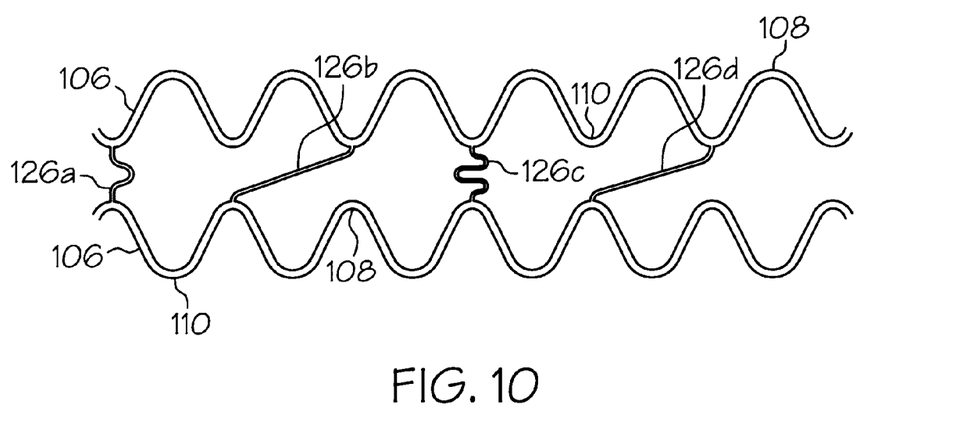
FIG. 10 shows several different interconnecting members which may be used in stents in accordance with the invention.
Figure 11:
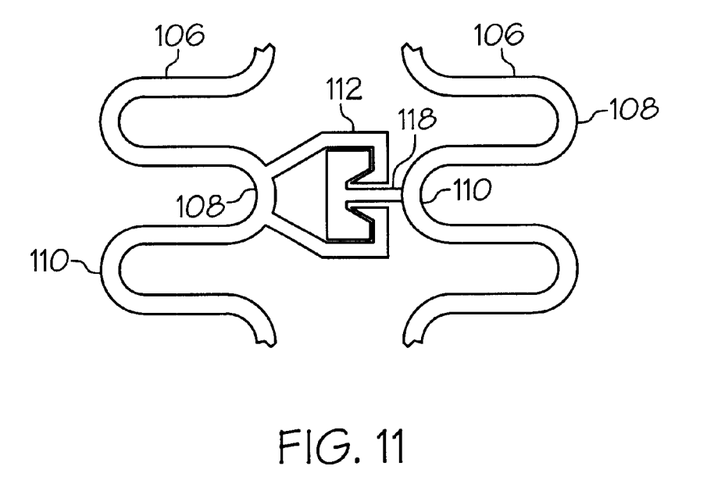
FIGS. 11 and 12 show a portion of a stent with interlocking members.
Figure 12:
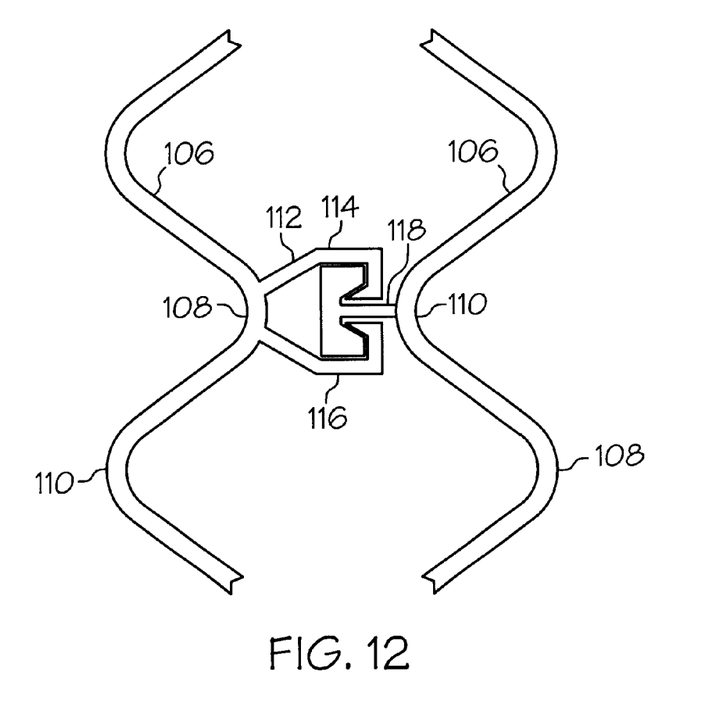

One such embodiment comprising a plurality of interconnected lockable cells may be realized by substituting the first and second interlocking members of FIGS. 10 and 11 for the pincer members and tongues of FIG. 1. As discussed above with respect to FIGS. 11 and 12, the second interlocking member is constructed and arranged to lockingly engage the first interlocking member on expansion of the stent.

Figure 15:
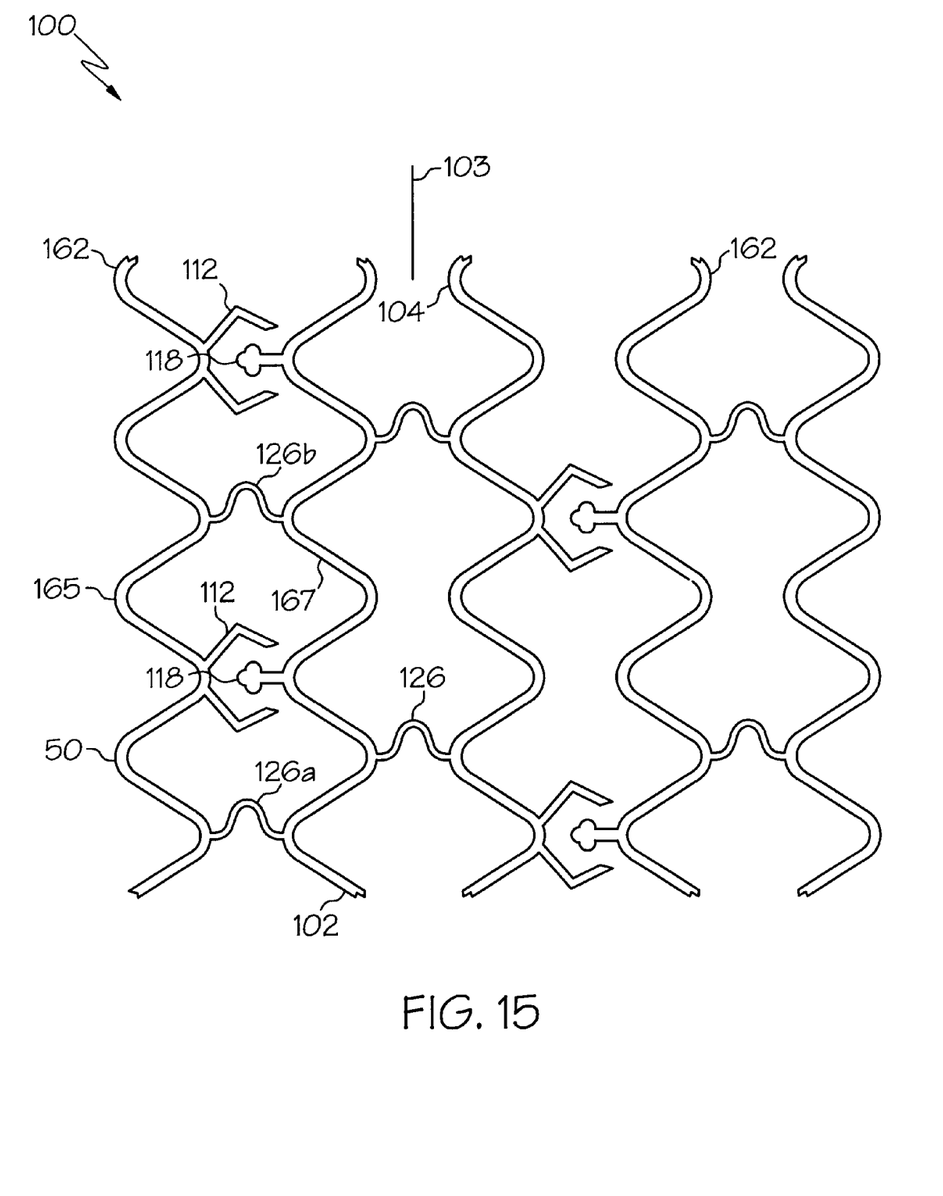
FIG. 15 illustrates a plan view of a stent having clamping members extending between longitudinal bands.

The invention is also directed to stents having longitudinal bands which may be locked together. As shown in FIG. 15, stent 100, having a proximal end 102 and a distal end 104, comprises a plurality of longitudinal bands 162. At least one of the longitudinal bands has at least one pincer member 112 extending therefrom and an adjacent longitudinal band has a tongue member extending therefrom toward pincer member 112. Desirably, a plurality of pincer members and tongues extend from adjacent longitudinal bands. Any of the other clamping members or interlocking members disclosed herein may also be used. Some adjacent longitudinal bands may have clamping or interlocking members extending therebetween or all adjacent longitudinal bands may have clamping or interlocking members extending therebetween. Adjacent longitudinal bands further have at least one other connector 126 extending there between and desirably a plurality of connectors therebetween. Adjacent longitudinal bands may also be connected by straight circumferential connectors or any of the connectors shown in FIG. 10. The stent of FIG. 15 is shown with five longitudinal bands. Additional or fewer longitudinal bands may be provided.

The invention contemplates providing serpentine longitudinal bands and/or non-serpentine longitudinal bands.

The invention is also directed to stents comprising at least one lockable cell and, desirably, a plurality of lockable cells having locking members. Desirably the locking members are clamping or interlocking members, extending from substantially longitudinally extending sidewalls. As shown in FIG. 15, cell 150 comprises a first substantially longitudinal sidewall 165, desirably serpentine, a second substantially longitudinal sidewall 167, desirably serpentine, a proximal wall 126a and a distal wall 126b. Pincer members 112 extends from first sidewall 165 and tongue member 118 extends from second sidewall 167 toward pincer member 112. On expansion of the stent, the pincer member clamps on the tongue.

Figure 16:
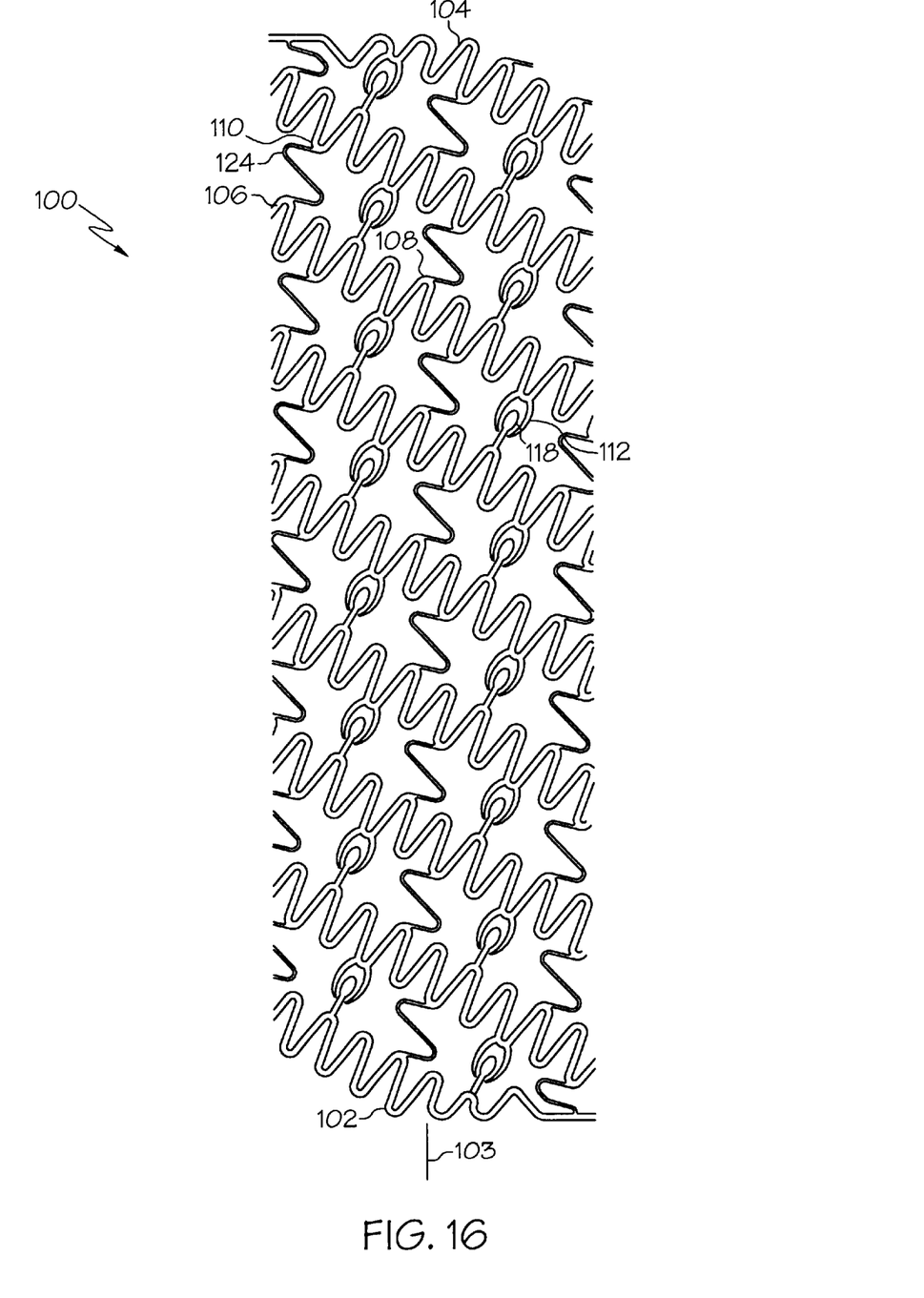
FIG. 16 illustrates an inventive helical stent.

The invention is also directed to helical stents having adjacent helical bands which may be locked together and to helical stents having one or more cells which have locking members. Desirably, the stent comprises clamping members or interlocking members. As shown in FIG. 16, helical stent 100, has a proximal end 102 and a distal end 104. Stent 100 comprises a serpentine band 106 which extends helically about longitudinal axis 103. Interconnecting members 124 extend from peaks 108 on a serpentine band to troughs 110 on adjacent helical turns of the serpentine band. Interconnecting members 124 may be replaced by any of the other interconnecting members shown in FIG. 10. The stent further comprises pincer members 112 and tongues 118. Pincer members 112 and tongues 118 may extend from peaks or troughs of the serpentine bands. Pincer members 112 are disposed opposite tongues 118 on adjacent helically extending serpentine bands. On expansion of the stent, the pincer members lock onto the tongues. Any of the other pincer members, tongues and interlocking members disclosed herein may also be used in the helical stent. Additional or fewer interconnecting members may be provided in the stent. Similarly, additional or fewer pincer member/tongue pairs or interlocking members may be provided.

The inventive helical stents may be made of a single serpentine band extending helically about the longitudinal axis of the stent or may be made of a plurality of serpentine bands helically extending about the longitudinal axis of the stent. Additionally, the inventive helical stents may be made of one or more non-serpentine bands extending helically about the longitudinal axis of the stent.

Figure 17:
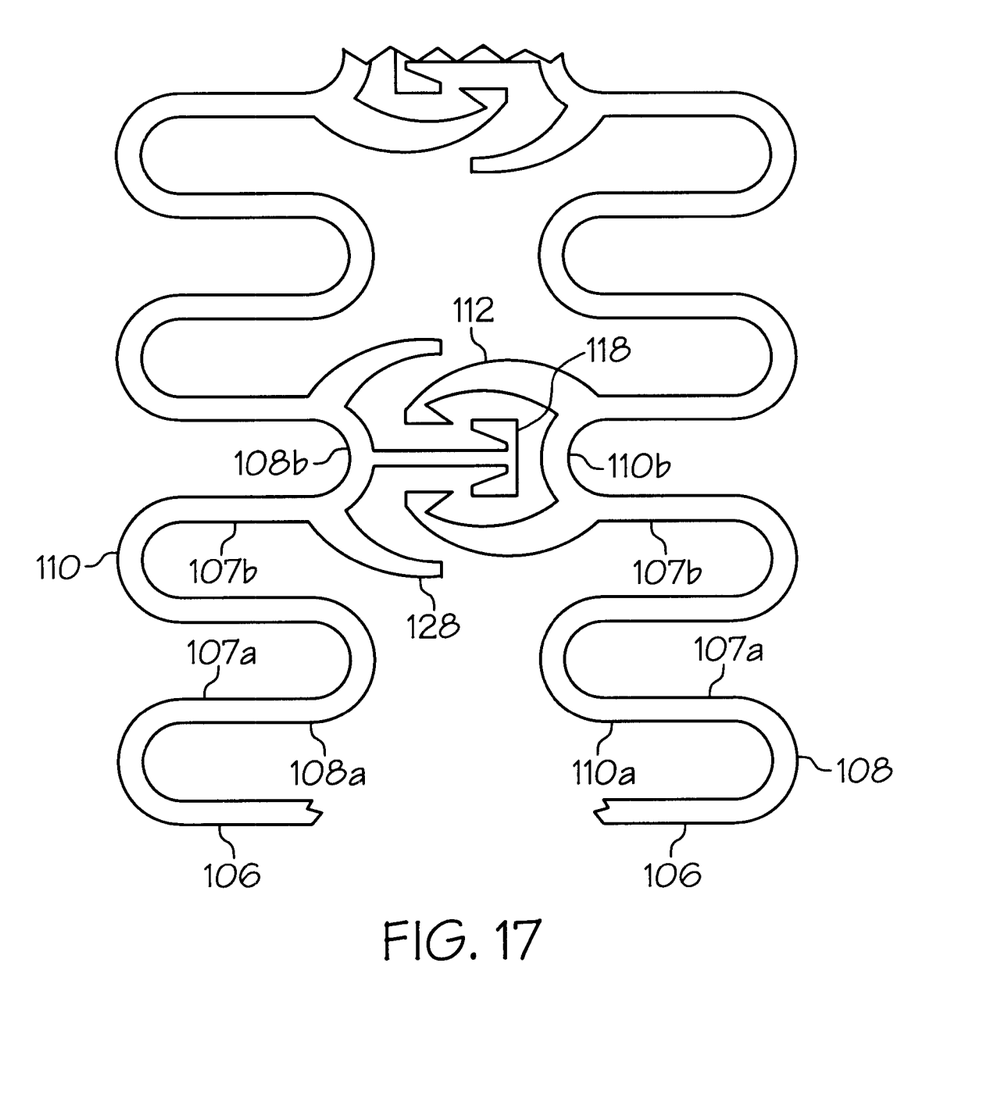
FIG. 17 illustrates a portion of a stent where the locking members lock prior to full expansion of the stent.

The invention is also directed to stents having locking members which lock prior to the complete expansion of the stent. This may be achieved by varying the thickness and/or width of peaks and/or troughs from which clamping members extend relative to the thickness and/or width of peaks and/or troughs from which no locking members extend or by varying the width or thickness of struts 107 which form serpentine bands 106 to control the expansion of the stent. In addition to varying As shown in FIG. 17, a portion of a stent is provided with bands 106 comprising peaks 108a from which no clamping members extend and peaks 108b from which clamping members 128 extend. Bands 106 further comprise troughs 110a from which no clamping members extend and troughs 110b from which clamping members 112 extend. Peaks 108a and troughs 110a from which no clamping members extend are wider than peaks 108b and troughs 110b from which clamping members extend. The narrower peaks 108b and troughs 110b will open prior to wider peaks 108a and troughs 110a. With such an arrangement and the appropriate relative widths, the clamping of the clamping members may be the first action during expansion of the stent.

With further reference to FIG. 17, clamping of the cells prior to complete expansion of the stent may also be achieved by modifying struts 107b relative to struts 107a. For example, struts 107b may be thinner or narrower than struts 107a.

As discussed above, the thickness of the peaks and troughs may also be varied. For example, a stent may be provided with thinner peaks and troughs with locking members extending therefrom and thicker peaks and troughs without any clamping members extending therefrom. The peaks and troughs from which locking members extend may also be subject to different treatments (whether heat treatment, chemical treatment or any other treatment) relative to the peaks and troughs from which no locking members extend to provide peaks and troughs with locking members which open before other peaks and troughs.

In one embodiment, the inventive stent consists entirely of bands such as those shown in FIG. 17 so that all of the locking members lock prior to complete expansion of the stent when the stent is expanded uniformly.

The invention also contemplates an embodiment in which the first and second locking members extend from peaks and troughs which open later, with peaks and troughs which open earlier not having any locking members extending therefrom. In this embodiment, the locking members lock as the expansion of the stent is completed.

In another embodiment, the stent is provided with a plurality of locking cells which require different amounts of force to lock. For example, the peaks from which locking members extend at the distal end of the stent may be narrower than the peaks from which locking members extend at the proximal end of the stent while the peaks from which no locking members expand may be wider at the distal end of the stent than at the proximal end of the stent. Assuming a uniform expansion of the stent, such a stent would lock at the distal end prior to at the proximal end.

The locking members whether clamping members or interlocking members or otherwise may be oriented in a longitudinal direction, in a circumferential direction or at an angle oblique to the longitudinal axis of the stent.

The invention also contemplates stents with locking members and interconnected bands whether circumferential, longitudinal, helical or otherwise where adjacent bands are dissimilar in frequency and/or amplitude.

More generally, the invention contemplates stents formed of any types of bands whether serpentine or otherwise and whether circumferential, longitudinal, helical or otherwise. The serpentine bands may be characterized by a single wavelength or by a plurality of wavelengths and may comprise interconnected struts of a single length or interconnected struts of a plurality of different lengths. Moreover, the serpentine bands may be characterized by a regular pattern or by an irregular patters. Bands having other geometric patterns that provide desirable contraction and expansion properties may be used as well. Examples of other types of bands that may be used include bands having openings therein of any suitable shape, including bands with triangular openings, diamond shaped openings, rectangular openings and more generally, polygonal openings, circular openings and more generally, openings having a curvilinear boundary. All of the bands in the stent may be identical or some or all of the bands may differ from one another. The bands may be characterized as having regular or irregular patterns. The stent may incorporate bands having a single wavelength and/or amplitude and/or bands having multiple wavelengths and/or amplitudes. The bands may also be non-serpentine, for example, purely circular.

Locking members may be disposed in longitudinal rows along the length of the stent or in helical patterns along the length of the stent or in any other pattern.

The various modifications to the structure of the inventive stents discussed above and below with respect to inventive stents comprising one or more pincer members may also be made to inventive stents comprising interlocking members and vice versa. Furthermore, any modifications of the structure discussed above and below with respect to the stent with clampable cell structures may also be made to an inventive stent with interlockable cells structure.

Any of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the bands may increase or decrease along portions of the stent or along the entire length of the stent.

The invention is also directed to bifurcated stents having locking. Both branches of a bifurcated stent may contain locking members or only a single branch may contain locking members. The relative rigidity of the branches of a bifurcated stent may also be controlled by providing different distributions of locking members in each of the branches. Thus, an inventive bifurcated stent may have two branches which are equally rigid or one branch which is more rigid than another branch. Bifurcated stents may also be provided with branches which require different amounts of force to lock.

The inventive stents may be manufactured using known stent manufacturing techniques including laser cutting, laser welding, chemically etching, electrode discharge machining or stamping a tube or a sheet. In the case of a sheet, the sheet is then rolled and welded. The inventive stents may also be molded with the desired design or may be made by growing or extruding or winding a stent with the inventive patterns.

Any suitable stent material may be used in the manufacture of the inventive stents. Examples of such materials include metals such as stainless steel, tantalum, elgiloy and shape memory metals such as nitinol. The inventive stents may also be made of suitable polymeric materials.

The inventive stents may include suitable radiopaque coatings. For example, the stents may be coated with gold or sputtered with tantalum. The stents may also be made directly from a radiopaque material to obviate the need for a radiopaque coating or may be made of a material having a radiopaque inner core.

The inventive stents may also be provided with various bio-compatible coatings to enhance various properties of the stent. For example, the inventive stents may be provided with lubricious coatings. The inventive stents may also be provided with drug-containing coatings which release drugs over time.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Subjecting the stent to such a treatment also may prevent flaring of the ends of the stent during delivery of the stent. Mechanical retention devices may also be used to maintain the stent on the balloon during delivery.

The inventive stents may be used inside the lumina of any physiological conduit including arteries, veins, vessels, the biliary tree, the urinary tract, the elementary tract, the tracheal bronchial tree, the genitourinary system, and the cerebral aqueduct.

In addition to the specific embodiments claimed below, the invention is also directed to other embodiments having any other possible combination of the dependent features claimed below.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent having a proximal end and a distal end, the stent comprising a plurality of interconnected cells, at least one of the interconnected cells being a lockable cell, the lockable cell including;

a first locking member and a second locking member disposed opposite the first member, the first and second locking members movable between a first position in which they do not lock with one another to a position in which they lock with one another; wherein the first locking member is a pincer member comprising a first arm and a second arm, and the second locking member is a tongue, the first arm and the second arm moving toward one another to grip the tongue on expansion of the stent.

2. The stent of claim 1 comprising a plurality of lockable cells, the lockable cells constructed and arranged so that the stent exhibits greater scaffolding strength when the stent is expanded.

3. The stent of claim 1, expandable from an unexpanded state to an expanded state, the first and second arms in the first position when the stent is in the unexpanded state, the first and second arms in the second position when the stent is in the expanded state.

4. The stent of claim 3 comprising a plurality of lockable cells.

5. The stent of claim 4 wherein the lockable cells are arranged in rows.

6. The stent of claim 5 wherein adjacent rows of lockable cells are connected by at least one connector member extending between the rows.

7. The stent of claim 4 comprising at least two types of lockable cells including
  at least one proximal lockable cell in which the pincer member is situated at a proximal end of the cell and the tongue is situated at the distal end of the cell; and
  at least one distal lockable cell in which the pincer member is situated at a distal end of the cell and the tongue is situated at the proximal end of the cell.

8. The stent of claim 1 wherein the lockable cell is a multiply lockable cell comprising a plurality of pincer members and a plurality of tongues.

9. The stent of claim 8 wherein one of the pincer members is situated at a distal end of the cell and one of the pincer members is located at a proximal end of the cell.

10. The stent of claim 9 comprising a plurality of multiply lockable cells.

11. The stent of claim 1, the lockable cell comprising a plurality of pincer members including
  a first pincer member comprising a first arm and a second arm and a tongue disposed between the first arm and the second arm and
  a second pincer member comprising a first arm and a second arm,
  the first pincer member situated opposite the second pincer member,
  wherein the first and second arms of the second pincer member grip the tongue of the first pincer member on expansion of the stent and the first and second arms of the second pincer member grips the first pincer member of the stent.

12. The stent of claim 1 wherein the lockable cell includes a serpentine shaped proximal end, a serpentine shaped distal end, a first sidewall extending between the serpentine shaped proximal end and the serpentine shaped distal end, and a second sidewall extending between the serpentine shaped proximal end and the serpentine shaped distal end, the tongue and the pincer member disposed between the first sidewall and the second sidewall.

13. The stent of claim 1 wherein the first locking member is an interlocking member and the second locking member is an interlocking member, the first and second interlocking members constructed and arranged to interlock with one another upon expansion of the stent.

14. A stent having a proximal end and a distal end, the stent comprising a plurality of interconnected cells, at least one of the interconnected cells being a lockable cell, the lockable cell including;
  a first locking member and a second locking member disposed opposite the first member, the first and second locking members movable between a first position in which they do not lock with one another to a position in which they lock with one another;
  the first locking member is a pincer member comprising a first arm and a second arm and the second locking member is a tongue,
  the first and second arms disposed in a first position in which they do not grip the tongue and movable between the first position and a second position in which they grip the tongue, the tongue including a narrow neck portion and a wider head portion.

15. A stent comprised of a plurality of interconnected bands,
  at least one of the interconnected bands having a first locking member extending therefrom toward an adjacent band, a second locking member extending from an adjacent band,
  the first and second locking members movable from a first position in which they do not lock with one another to a second position in which they lock with one another; wherein
  the first locking member is a pincer member comprising a first arm and a second arm, and the second locking member is a tongue,
  the first arm and the second arm moving toward one another to grip the tongue on expansion of the stent.

16. The stent of claim 15 wherein the first locking member is a pincer member having a first arm and a second arm and the second locking member is a tongue extending from the adjacent band, the first and second arms gripping the tongue in the second position.

17. The stent of claim 16 expandable from an unexpanded state to an expanded state, the first and second arms in the first position when the stent is in the unexpanded state, the first and second arms in the second position when the stent is in the expanded state.

18. The stent of claim 17 wherein each band is serpentine having alternating peaks and troughs, the peaks extending in a distal direction, the troughs extending in a proximal direction.

19. The stent of claim 18 wherein the pincer member extends from a peak on a band and the tongue extends from a trough on an adjacent band.

20. The stent of claim 16, at least one of the interconnected bands having a plurality of pincer members extending therefrom toward an adjacent band,
  each pincer member having a first arm and a second arm,
  the adjacent band having a plurality of tongues extending therefrom,
  the first and second arms of each pincer member movable between a first position in which they are not in contact with one of the tongues and a second position in which they grip one of the tongues.

21. The stent of claim 16, wherein a plurality of bands each have at least one pincer member extending therefrom toward a tongue extending from an adjacent band.

22. The stent of claim 15 wherein the bands extend circumferentially.

23. The stent of claim 15 wherein the bands extend longitudinally.

24. The stent of claim 15 wherein the bands extend helically.

25. The stent of claim 16 the adjacent band comprising a second pincer member which comprises a first arm and a second arm, the tongue disposed between the first and second arms of the second pincer member,
  the first pincer member situated opposite the second pincer member,
  wherein the first and second arms of the second pincer member grip the tongue of the first pincer member on expansion of the stent and the first and second arms of the second pincer member grips the first pincer member of the stent.

26. The stent of claim 15 wherein the first locking member is a first interlocking member and the second locking member is a second interlocking member, the first and second interlocking members constructed and arranged to interlock with one another upon expansion of the stent.

27. A stent comprised of a plurality of interconnected bands,
  at least one of the interconnected bands having a first locking member extending therefrom toward an adjacent band, a second locking member extending from an adjacent band, the first and second locking members movable from a first position in which they do not lock with one another to a second position in which they lock with one another, the first locking member is a pincer member having a first arm and a second arm and the second locking member is a tongue extending from the adjacent band, the first and second arms gripping the tongue in the second position, the tongue including a narrow neck portion and a wider head portion.

28. A stent having a proximal end and a distal end, the stent comprising a plurality of interconnected cells, at least one of the interconnected cells being a lockable cell, the lockable cell including a first locking member and a second locking member, the second locking member constructed and arranged to lockingly engage the first locking member on expansion of the stent, wherein the first locking member is a pincer member comprising a first arm and a second arm, and the second locking member is a tongue, the first arm and the second arm moving toward one another to grip the tongue on expansion of the stent.

29. The stent of claim 28 comprising a plurality of lockable cells.

30. The stent of claim 29 comprising rows of lockable cells and at least one row of non-lockable cells.

31. The stent of claim 30 comprising a plurality of rows of non-lockable cells, wherein the rows of lockable cells alternate with the rows of non-lockable cells along the length of the stent.

32. The stent of claim 30 where at least one row of lockable cells is provided at one of the distal end of the stent and the proximal end of the stent.

33. The stent of claim 30 wherein at least one row of lockable cells is provided between the proximal and distal ends of the stent.

34. The stent of claim 28 wherein the number of lockable cells disposed about the periphery of the stent increases from one end of the stent to the other.

35. The stent of claim 28 wherein the first locking member clamps to the second locking member on expansion of the stent.

36. The stent of claim 28 wherein the first locking member and the second locking member interlock with one another.

37. An unexpanded stent comprised of a plurality of connected bands at least one of the bands having a first locking member extending therefrom toward an adjacent band, the adjacent band having a second locking member, the second locking member lockingly engaging the first locking member when the stent is in an expanded state, wherein the first locking member is a pincer member comprising a first arm and a second arm, and the second locking member is a tongue, the first arm and the second arm moving toward one another to grip the tongue on expansion of the stent.

38. The stent of claim 37 wherein the first locking member is a first interlocking member and the second locking member is a second interlocking member, the second interlocking member constructed and arranged to interlock with the first interlocking member on expansion of the stent.

39. The stent of claim 38 plurality of the bands each having at least one first interlocking member extending therefrom toward a second interlocking member extending from an adjacent band, wherein the first interlocking member is a female member and the second interlocking member is a male member.

40. The stent of claim 37 wherein at least one of the proximal end of the stent and the distal end of the stent are provided with first and second locking members which are positioned to be lockable.

41. The stent of claim 37 wherein the number of first locking members increases from one end of the stent to the other end of the stent.

42. The stent of claim 37 wherein the bands are non-serpentine in shape.

43. The stent of claim 37 wherein the bands are serpentine and comprise stronger and weaker peaks and stronger and weaker troughs, the first and second locking members extending from the weaker peaks and troughs.

44. The stent of claim 37 wherein the bands are serpentine and comprise peaks and troughs which open earlier and peaks and troughs which open later on expansion of the stent, the first and second locking members extend from the peaks and troughs which open earlier.

* * * * *